(12) United States Patent
Kouzarides

(10) Patent No.: US 6,890,709 B1
(45) Date of Patent: May 10, 2005

(54) ASSAYS, METHODS AND MEANS FOR MODULATING E2F ACTIVITY

(75) Inventor: Tony Kouzarides, Cambridge (GB)

(73) Assignee: Chroma Therapeutics Limited, Oxfordshire (GB)

( * ) Notice: Subject to any disclaimer, the term of this patent is extended or adjusted under 35 U.S.C. 154(b) by 0 days.

(21) Appl. No.: 09/700,417

(22) PCT Filed: May 17, 1999

(86) PCT No.: PCT/GB99/01571

§ 371 (c)(1),
(2), (4) Date: Nov. 29, 2000

(87) PCT Pub. No.: WO99/60407

PCT Pub. Date: Nov. 25, 1999

(30) Foreign Application Priority Data

May 17, 2000 (DE) .............................. 9810582

(51) Int. Cl.$^7$ .............................. C12Q 1/00; C12Q 1/68; C12Q 33/53
(52) U.S. Cl. ................................ 435/4; 435/6; 435/7.1
(58) Field of Search ...................... 435/4, 6, 7.1; 514/2, 514/44; 530/300, 358

(56) References Cited

FOREIGN PATENT DOCUMENTS

| WO | 97/35975 | 10/1997 |
|----|----------|---------|
| WO | 97/35990 | 10/1997 |
| WO | 98/03652 | 1/1998 |

OTHER PUBLICATIONS

Hartwell et al, Science, 1994, vol. 266, pp. 1821–1828.*
Ferreira et al, PNAS, 1998, vol. 95, pp. 10493–10498.*
Nevins et al, Science, 1992, vol. 258, pp. 424–429.*
Bargou et al, Journal of Experimental Medicine, 1996, vol. 183, pp. 1205–1213.*
Trouche et al, Nucleic Acids Research, 1996, vol. 24, pp. 4139–4145.*
Bandara L R et al.: "Functional Synergy Between DP–1 and E2F–1 in the Cell Cycle–Regulating Transcription Factor DRTF1/E2F" EMBO Journal, vol. 12, No. 11, (Jan. 1993) pp. 4317–4324.
Adams P D et al.: "Transcriptional Control By E2F" Seminars in Cancer Biology, vol. 6, No. 2, (Apr. 1995) pp. 99–108.
Yang X–J et al.: "A P300/CBP–Associated Factor that Competes with the Adenoviral Oncoporotein E1A" Nature, vol. 382, No. 8589, (Jul. 1996) pp. 319–324.
LAM EWF et al.: "An E2F–Binding Site Mediates Cell–Cycle Regulated Repression of Mouse B–myb Transcription" EMBO Journal, vol. 7, No. 12, (Jan. 1993) pp. 2705–2713.

* cited by examiner

Primary Examiner—Karen A. Canella
(74) Attorney, Agent, or Firm—Nixon & Vanderhye P.C.

(57) ABSTRACT

P/CAF interacts with and acetylates E2F, this acetylation affecting ability of E2F to stimulate transcription. Interaction between P/CAF and E2F and acetylation of E2F by P/CAF are modulated, affecting ability of E2F to stimulate transcription, induction of S-phase in cells, oncogenicity of cells, and induction of apoptosis in cells. Agents are obtained for treatment of disorders of cell growth.

10 Claims, No Drawings

ASSAYS, METHODS AND MEANS FOR MODULATING E2F ACTIVITY

This application is the U.S. national phase of international application PCT/GB99/01571 filed 17 May 1999, which designated the U.S. PCT/GB99/01571 claims priority to GB Application No. 9810562.0 filed 15 May 1998.

The present invention relates to screening methods, peptides, mimetics, and methods of use based on the surprising discovery and characterisation of an interaction between known proteins, and thus numerous cellular processes of interest in therapeutic contexts. The proteins in question are P/CAF and E2F, it further being shown herein that P/CAF acetylates E2F at residues affecting ability of E2F to stimulate transcription. Prior to the making of the present invention it was not known that acetylation of E2F affects its activity, in particular its transcriptional activation, nor that P/CAF interacts with and acetylates E2F, thereby, affecting transcriptional activation by E2F.

The DNA in the nucleus is wrapped around a histone-core which is a protein complex involving the four histones H4, H3, H2B and H2A. This DNA-histone structure (nucleosome) is not compatible with gene expression. Re-organisation of the nucleosome is required for transcription factors and RNA polymerase to have access to the DNA for transcription.

Acetylation of histones at specific lysine residues has been correlated with an increase in gene expression. This modification is thought to re-model the nucleosomes and therefore increase the transcription of a given template DNA. In the last two years enzymes have been identified which carry out this acetylation of histones. There are now four families of enzymes with such activity. These are GCN5 and P/CAF (Brownell, et al (1996), *Cell,* 84: 843–831 and Yang, et al (1996), *Nature,* 382: 319–324), CBP and p300 (Bannister and Kouzarides (1996), *Nature,* 384: 641–643 and Ogryzko, et al (1996), *Cell,* 87: 953–959), SRC1 and ACTR (Chen, et al (1997), *Cell,* 90: 569–580 and Spencer, et al (1997), *Nature,* 389: 194–198) and TAF250 (Mizzen, et al (1996), Cell, 87: 1261–1270). The precise in vivo targets of these enzymes are not known. In vitro experiments suggest that recombinant enzymes may have specificity for distinct lysines within the same histone. Precisely how acetylation of a particular histone increases transcription is not known.

Recently, evidence has been provided that some proteins other than histones are acetylated. The p53 transcription factor and the basal transcription factors TFIIE and TFIIF have been shown to be acetylated (Imhof, et al (1997), *Current Biology,* 7: 689–692). In the case of p53 it has been shown that acetylation increases the DNA binding capacity of the protein.

The present invention is based on the surprising discovery that P/CAF interacts with and acetylates E2F and that the acetylated residues are important for E2F function.

Experimental work on this is described below and leads to various aspects of the present invention in which there is provided for modulation of interaction between P/CAF and E2F, particularly acetylation of E2F by P/CAF.

Various aspects of the present invention provide for the use of P/CAF and E2F, with or without DNA, in screening methods and assays for agents which modulate interaction between P/CAF and E2F, particularly acetylation of E2F by P/CAF, and agents which modulate the ability of E2F to stimulate transcription and/or the function of E2F in induction of S-phase, oncogenicity and/or induction of apoptosis.

Identification of key residues in E2F acetylated by P/CAF may also be used in the design of peptide and non-peptidyl agents which modulate, particularly inhibit, acetylation of E2F by P/CAF or other acetylase enzyme, as discussed further below.

Methods of obtaining agents able to modulate interaction between P/CAF and E2F include methods wherein a suitable end-point is used to assess interaction in the presence and absence of a test substance. Assay systems may be used to determine P/CAF acetylase activity and/or P/CAF interaction with E2F and/or acetylation of E2F by one or more other acetylases. For acetylation assays, full-length E2F, truncated portions of E2F, or portions of E2F fused to other proteins (eg. GST), or a suitable variant or derivative of any of these may be used. Peptide acetylation assays may be developed using peptides that correspond to the acetylated regions of E2F. The acetylation of any of the above may be assayed by any of a variety of procedures such as discussed below and may be adapted to high throughput screening approaches. Generally of most interest is modulation of the acetylation of E2F by P/CAF or other acetylase. Detailed disclosure in this respect is included below. It is worth noting, however,, that combinatorial library technology provides an efficient way of testing a potentially vast number of different substances for ability to modulate an interaction with and/or activity of a polypeptide. Such libraries and their use are known in the art, for all manner of natural products, small molecules and peptides, among others. The use of peptide libraries may be preferred in certain circumstances.

Given the results reported herein on which the present invention is based, activators and inhibitors of P/CAF-associated acetylase activity or other acetylase able to acetylate E2F may be identified and appropriate agents may be obtained, designed and used for any of a variety of purposes. Modulation of E2F function may be used for the control of cell proliferation. E2F1 is known to be oncogenic (Johnson, et al (1994), *PNAS:* 91, 12823–12827 and Singh, et al (1994), *EMBO: Vol* 13, No 14, 3329–3338) and is able to induce S-phase when microinjected into cells (Johnson, et al, *Nature:* 365, 349–352). The ubiquitous expression of E2F makes it a good candidate target for modulation of growth control in a number of neoplasias, tumours, cancer, psoriasis, arteriosclerosis and other hyper-proliferative disorders. Overexpression of E2F1 can cause cell death (apoptosis) (Shan and Lee, *Molecular and Cellular Biology:* Vol 14, No 12, 8166–8173) and modulation of E2F function in accordance with the present invention may be used to induce apoptosis.

Thus, various methods and uses of modulators, which inhibit or potentiate interaction of P/CAF and E2F, and modulators that affect acetylation of E2F, are provided as further aspects of the present invention. The purpose of disruption, interference with or modulation of interaction between P/CAF and E2F, particularly the acetylation of E2F by P/CAF may be to modulate any activity mediated by virtue of such interaction, as discussed above and further below.

Acetylation of E2F by one or more other acetylases may be modulated for the same or similar purposes.

The full amino acid sequence of the P/CAF protein has been elucidated and is set out in Yang, et al, *Nature:* 382, 319–324. Residues 352–658 of P/CAF have been shown to include P/CAF histone acetyltransferase activity. Within this region is a stretch of about 100 residues homologous to CBP (another histone acetyltransferase). Point mutations within P/CAF which eliminate the acetyltransferase activity are disclosed in Martinez-Balbás, et al, *EMBO:* Vol 17, 101–108.

The E2F/DP family of transcription factors play a key role in regulating the mammalian cell cycle. They activate genes required for S-phase and in doing so can ultimately promote cell proliferation. Both E2F and DP family members have been shown to be oncogenic and E2F1 has been demonstrated to be a potent inducer of S-phase (Lam, E. W-F. et al. Current Opinion in Cell Biology 1994, 6: 859–866).

The transcription activation capacity (and hence the oncogenicity) of the E2F/DP family is kept in check by the Retinoblastoma tumour suppressor family of proteins (RB, p107, 0130). Members of this family bind to a transcriptional activation domain within the E2F protein. By doing so, the RB protein family members can silence the transcriptional activation capacity of the E2F/DP proteins and thus cause arrest in the G1-phase of the cell cycle. Release of RB from E2F/DP results in S-phase induction. This release is mediated by phosphorylation events (on RB and E2F) carried out by cyclin/CDK complexes towards the end of the G1 phase (Whyte, P. The retinoblastoma protein and its relatives. Seminars in Cancer Biology 1995, 6: 83–90).

There are five identified members of the E2F family (E2F1–5) and three members of the DP family (DP1–3). All E2F members can form heterodimers with all DP members. These heterodimers can bind and transactivate the promoters of S-phase genes.

The E2F and DP proteins share a common class of DNA binding and dimerisation domain which allows them to form heterodimers and bind "E2F" binding sites co-operatively. Outside the DNA binding/dimerisation domain the E2F family members have other sequences in common. They all have a highly conserved "marked box", whose function is unknown, and a transcriptional activation domain at the C-terminus which contains the binding site for the RB family of proteins. DP family of proteins do not possess any similarity to E2F proteins outside the DNA binding domain. However, they do contain highly conserved sequences which define this family.

The activity of the various E2F/DP heterodimers comes from the transcriptional activity of the E2F partner. No activation functions have been attributed to DP proteins. The activation capacity of the E2F/DP complexes is negatively regulated by different members of the RB family: RB binds and represses E2F1–3 whereas p107 and p130 can bind and repress E2F4 and E2F5. Brehm et al. (1998) *Nature* 391: 597–601 and Magnaghi-Jaulin et al. (1998) *Nature* 391: 601–605 show that the Retinoblastoma protein Rb recruits histone deacetylase to E2F, cooperating with the histone deacetylase to repress transcription from E2F-regulated promoters.

An agent capable of modulating interaction between P/CAF and E2F may be capable of blocking interaction between P/CAF and one or more of the lysine residues in the various E2F's as follows, the alignment providing indication of significant homology between E2F1, E2F2 and E2F3:

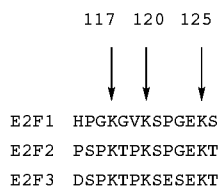

```
        117 120 125
         ↓   ↓   ↓
E2F1  HPGKGVKSPGEKS
E2F2  PSPKTPKSPGEKT
E2F3  DSPKTPKSESEKT
```

Reference to acetylation of E2F generally applies herein unless context requires otherwise to any of the E2F's, but particularly E2F1, E2F2 and/or E2F3, and most particularly E2F1.

In addition to interacting at the site of acetylation of E2F, P/CAF and E2F may interact at one or more other sites within either or both proteins. Affecting interaction at such a site may have an effect on acetylation of E2F by P/CAF. Various fragments and derivatives of the proteins, particularly of E2F, may be used to analyse this, using techniques such as alanine scanning and deletion analysis. The present invention encompasses modulation of interaction between P/CAF and E2F at any site, preferably resulting in modulation of E2F acetylation.

Other agents according to the present invention useful in modulating acetylation of E2F and therefore one or more of its functions modulate the acetyltransferase activity of the acetylase. Such agents may specifically inhibit the ability of P/CAF to acetylate E2F. Assays and screens for such agents are provided in accordance with the present invention, along with the agents themselves and their use in modulating E2F acetylation and in modulating E2F function.

Agents useful in accordance with the present invention may be identified by screening techniques which involve determining whether an agent under test inhibits or disrupts the interaction of P/CAF protein or a suitable fragment thereof (e.g. including amino acid residues of the acetylase domain, or a smaller fragment of any of these regions) of P/CAF, with E2F or a fragment thereof, or a suitable analogue, fragment or variant thereof.

Suitable fragments of P/CAF or E2F include those which include residues which interact with the counterpart protein. Smaller fragments, and analogues and variants of this fragment may similarly be employed, e.g. as identified using techniques such as deletion analysis or alanine scanning.

Thus, the present invention provides a peptide fragment of P/CAF which is able to interact with E2F and/or inhibit interaction between P/CAF and E2F, particularly acetylation of E2F by P/CAF, and provides a peptide fragment of E2F which is able to interact with P/CAF and/or inhibit interaction between E2F and P/CAF, particularly acetylation of E2F by P/CAF, such peptide fragments being obtainable by means of deletion analysis and/or alanine scanning of the relevant protein—making an appropriate mutation in sequence, bringing together a mutated fragment of one of the proteins with the other or a fragment thereof and determining interaction, preferably acetylation of E2F or fragment thereof. In preferred embodiments, the peptide is short, as discussed below, and may be a minimal portion that is able to interact with the relevant counterpart protein and/or inhibit the relevant interaction. The invention further provides peptide fragments of E2F which are able to inhibit acetylation of E2F at the relevant residues.

Other proteins may bind E2F at an acetylation site, and may bind or not depending on whether the site is acetylated or not. A protein other than P/CAF may bind at any one or more of the relevant lysines when they are acetylated, but not when not acetylated. A protein other than P/CAF may bind at any one or more of the relevant lysines when they are not acetylated, but not when acetylated. Such proteins may be identified using standard methodology to identify interacting proteins. For instance, non-acetylated E2F fragments may be used in two-hybrid screens and chemically acetylated peptides may be screened against peptide and protein libraries. The invention further extends to the use of E2F and peptide fragments thereof including one or more of the relevant lysines, acetylated or not acetylated, for obtaining a peptide or protein (other than P/CAF) which binds at an acetylation site, particular a peptide or protein which binds or not depending on whether the site is acetylated or not. Further aspects of the invention provide assay methods for such peptides and proteins based on determining binding to E2F or a peptide fragment thereof, acetylated or not acetylated at one or more of the relevant lysines. The invention further extends to assays for substances able to modulate interaction of such peptides or proteins with the relevant acetylation site, and to methods of modulating such interaction, also modulating agents.

Peptides in accordance with the present invention tend to be short, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6, 5 or less in length. Peptides according to the present invention may be about 10–40 amino acids in length, about 5–10, about 10–15, about 10–20, about 10–30, about 20–30, or about 30–40 amino acids in length. Peptides which are E2F fragments may include one or more of the relevant lysine residues noted above (e.g. for E2F1 Lys117, Lys120 and/or Lys125).

The present invention also encompasses peptides which are sequence variants or derivatives of a wild type P/CAF or E2F sequence, but which retain ability to interact with E2F or P/CAF (respectively, as the case may be) and/or ability to modulate interaction between P/CAF and E2F, particularly acetylation of E2F by P/CAF, and/or ability to modulate acetylation of E2F by one or more other acetylases.

Instead of using a wild-type P/CAF or E2F fragment, a peptide or polypeptide may include an amino acid sequence which differs by one or more amino acid residues from the wild-type amino acid sequence, by one or more of addition, insertion, deletion and substitution of one or more amino acids. Thus, variants, derivatives, alleles, mutants and homologues, e.g. from other organisms, are included.

Preferably, the amino acid sequence shares homology with a fragment of the relevant P/CAF or E2F fragment sequence shown preferably at least about 30%, or 40%, or 50%, or 60%, or 70%, or 75%, or 80%, or 85%, 90% or 95% homology. Thus, a peptide fragment of P/CAF or E2F may include 1, 2, 3, 4, 5, greater than 5, or greater than 10 amino acid alterations such as substitutions with respect to the wild-type sequence.

A derivative of a peptide for which the specific sequence is disclosed herein may be in certain embodiments the same length or shorter than the specific peptide. In other embodiments the peptide sequence or a variant thereof may be included in a larger peptide, as discussed above, which may or may not include an additional portion of P/CAF or E2F. 1, 2, 3, 4 or 5 or more additional amino acids, adjacent to the relevant specific peptide fragment in P/CAF or E2F, or heterologous thereto may be included at one end or both ends of the peptide.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or more preferably using the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Homology may be over the full-length of the relevant polypeptide or may more preferably be over a contiguous sequence of about 15, 20, 25, 30, 40, 50, 75, 100 or more amino acids, compared with the relevant wild-type amino acid sequence.

At the nucleic acid level sequence identity may be assessed by means of hybridization of molecules under stringent conditions. The present invention extends to nucleic acid that hybridizes with any one or more of the specific sequences disclosed herein under stringent conditions. Suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

As noted, variant peptide sequences and peptide and non-peptide analogues and mimetics may be employed, as discussed further below.

Various aspects of the present invention provide a substance, which may be a single molecule or a composition including two or more components, which includes a peptide fragment of P/CAF, particularly within the P/CAF acetylase domain, or E2F, particularly within the acetylated region of E2F, a peptide consisting essentially of such a sequence, a peptide including a variant, derivative or analogue sequence, or a non-peptide analogue or mimetic which has the ability to interact with P/CAF or E2F and/or modulate, disrupt or interfere with interaction between P/CAF and E2F.

Variants include peptides in which individual amino acids can be substituted by other amino acids which are closely related as is understood in the art and indicated above.

Non-peptide mimetics of peptides are discussed further below.

As noted, a peptide according to the present invention and for use in various aspects of the present invention may include or consist essentially of a fragment of P/CAF or E2F respectively. Where one or more additional amino acids are included, such amino acids may be from P/CAF or E2F or may be heterologous or foreign to P/CAF or E2F. A peptide may also be included within a larger fusion protein, particularly where the peptide is fused to a non-P/CAF or non-E2F (i.e. heterologous or foreign) sequence, such as a polypeptide or protein domain.

The invention also includes derivatives of the peptides, including the peptide linked to a coupling partner, e.g. an effector molecule, a label, a drug, a toxin and/or a carrier or transport molecule, and/or a targeting molecule such as an antibody or binding fragment thereof or other ligand. Techniques for coupling the peptides of the invention to both peptidyl and non-peptidyl coupling partners are well known in the art. In one embodiment, the carrier molecule is a 16 aa peptide sequence derived from the homeodomain of Antennapedia (e.g. as sold under the name "Penetratin"), which can be coupled to a peptide via a terminal Cys residue. The "Penetratin" molecule and its properties are described in WO 91/18981.

Peptides may be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion an& then, if desired and appropriate, after removal of any protecting groups being present, by introduction of the residue X by reaction of the respective carbonic or sulfonic acid or a reactive derivative thereof.

Another convenient way of producing a peptidyl molecule according to the present invention (peptide or polypeptide) is to express nucleic acid encoding it, by use of nucleic acid in an expression system.

Accordingly the present invention also provides in various aspects nucleic acid encoding the polypeptides and peptides of the invention.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a polypeptide or peptide in accordance with the present invention can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992), given the nucleic acid sequence and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding P/CAF or E2F fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the P/CAF or E2F sequences can be made, e.g. using site directed mutagenesis, to lead to the expression of modified P/CAF or E2F peptide or to take account of codon preference in the host cells used to express the nucleic acid.

In order to obtain expression of the nucleic acid sequences, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of E. coli, yeast, and eukaryotic cells such as COS or CHO cells.

Thus, the present invention also encompasses a method of making a polypeptide or peptide (as disclosed), the method including expression from nucleic acid encoding the polypeptide or peptide (generally nucleic acid according to the invention). This may conveniently be achieved by growing a host cell in culture, containing such a vector, under appropriate conditions which cause or allow expression of the polypeptide. Polypeptides and peptides may also be expressed in in vitro systems, such as reticulocyte lysate. Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing heterologous nucleic acid as disclosed herein.

The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below)

Introduction of nucleic acid encoding a peptidyl molecule according to the present invention may take place in vivo by way of gene therapy, to disrupt or interfere with interaction between P/CAF and E2F or otherwise affect E2F acetylation.

Thus, a host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) Also, the presence of a mutant, allele, derivative or variant sequence within cells of an organism, particularly when in place of a homologous endogenous sequence, may allow the organism to be used as a model in testing and/or studying substances which modulate activity of the encoded polypeptide in vitro or are otherwise indicated to be of therapeutic potential. Knock-out mice, for instance, may be used to test for radiosensitivity. Conveniently, however, at least preliminary assays for such substances may be carried out in vitro, that is within host cells or in cell-free systems.

Where an effect of a test compound is established on cells in vitro, those cells or cells of the same or similar type may be grafted into an appropriate host animal for in vivo testing.

For instance, E2F function or activity may be measured in an animal system such as a tumour model, e.g. involving a xenograft, relying on active E2F.

Suitable screening methods are conventional in the art. They include techniques such as radioimmunosassay, scintillation proximetry assay and ELISA methods. Suitably either the P/CAF protein or fragment or E2F or fragment, or an analogue, derivative, variant or functional mimetic thereof, is immobilised whereupon the other is applied in the presence of the agents under test. In a scintillation proximetry assay a biotinylated protein fragment may be bound to streptavidin coated scintillant—impregnated beads (produced by Amersham). Binding of radiolabelled peptide is then measured by determination of radioactivity induced scintillation as the radioactive peptide binds to the immobilized fragment. Agents which intercept this are thus inhibitors of the interaction. Further ways and means of screening for agents which modulate interaction between P/CAF and E2F are discussed below.

In one general aspect, the present invention provides an assay method for an agent with ability to modulate, e.g. disrupt or interfere with interaction between P/CAF and E2F, the method including:

(a) bringing into contact a first substance including a peptide fragment of P/CAF or a derivative, variant or analogue thereof as disclosed, a second substance including the relevant fragment of E2F or a variant, derivative or analogue thereof, and a test compound under conditions in which, in the absence of the test compound being an inhibitor, the first and second substances interact; and (b) determining interaction between the first and second substances.

A test compound which disrupts, reduces, interferes with or wholly or partially abolishes interaction between said substances (e.g. including a P/CAF fragment and including a E2F fragment), and which may modulate P/CAF and/or E2F activity, may thus be identified.

Agents which increase or potentiate interaction between the two substances may be identified using conditions which, in the absence of a positively-testing agent, prevent the substances interacting. As noted, such agents may be used to potentiate E2F function, for instance in inducing apoptosis.

Another general aspect of the present invention provides an assay method for a substance able to interact with the relevant region of P/CAF or E2F as the case may be, the method including:

(a) bringing into contact a substance which includes a peptide fragment of P/CAF which interacts with E2F, or which includes a peptide fragment of E2F which interacts with P/CAF, or a variant, derivative or analogue of such peptide fragment, as disclosed, and a test compound; and (b) determining interaction between said substance and the test compound.

A test compound found to interact with the relevant portion of P/CAF may be tested for ability to modulate, e.g. disrupt or interfere with, P/CAF interaction with E2F and/or ability to affect E2F and/or P/CAF activity or other activity mediated by P/CAF or E2F as discussed already above.

Similarly, a test compound found to interact with the relevant portion of E2F may be tested for ability to modulate, e.g. disrupt or interfere with, E2F interaction with P/CAF and/or ability to affect P/CAF and/or E2F activity or other activity mediated by E2F or P/CAF as discussed elsewhere herein.

Another general aspect of the present invention provides an assay method for a substance able to affect E2F activity, the method including:

(a) bringing into contact E2F and a test compound; and (b) determining E2F activity (e.g. ability to activate transcription from an appropriate promoter, ability to induce S-phase, or ability to induce apoptosis).

E2F activity may be determined in the presence and absence of P/CAF to allow for an effect of a test compound on activity to be attributed to an effect on interaction between E2F and P/CAF, preferably acetylation of E2F by P/CAF (discussed further below).

Assays for E2F transcriptional activation are standard in the art. See e.g. Van Der Eb and Graham, Methods Enzymol: 65, 826–839.

The precise format of an assay of the invention may be varied by those of skill in the art using routine skill and knowledge. For example, interaction between substances may be studied in vitro by labelling one with a detectable label and bringing it into contact with the other which has been immobilised on a solid support. Suitable detectable labels, especially for peptidyl substances include $^{35}$S-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of an in vivo assay. The in vivo assay may be performed in a cell line such as a yeast strain or mammalian cell line in which the relevant polypeptides or peptides are expressed from one or more vectors introduced into the cell.

The ability of a test compound to modulate interaction between P/CAF and E2F may be determined using a so-called two-hybrid assay.

For example, a polypeptide or peptide containing a fragment of P/CAF or E2F as the case may be, or a peptidyl analogue or variant thereof as disclosed, may be fused to a DNA binding domain such as that of the yeast transcription factor GAL 4. (A particularly preferred fragment of P/CAF may include or be the acetylase domain or a fragment of the acetylase domain.) The GAL 4 transcription factor includes two functional domains. These domains are the DNA binding domain (GAL4DBD) and the GAL4 transcriptional activation domain (GAL4TAD). By fusing one polypeptide or peptide to one of those domains and another polypeptide or peptide to the respective counterpart, a functional GAL 4 transcription factor is restored only when two polypeptides or peptides of interest interact. Thus, interaction of the polypeptides or peptides may be measured by the use of a reporter gene probably linked to a GAL 4 DNA binding site which is capable of activating transcription of said reporter gene. This assay format is described by Fields and Song, 1989, Nature 340; 245–246. This type of assay format can be used in both mammalian cells and in yeast. Other combinations of DNA binding domain and transcriptional activation domain are available in the art and may be preferred, such as the LexA DNA binding domain and the VP60 transcriptional activation domain.

When looking for peptides or other substances which interfere with interaction between a P/CAF polypeptide or peptide and E2F polypeptide or peptide, the P/CAF or E2F polypeptide or peptide may be employed as a fusion with (e.g.) the LexA DNA binding domain, and the counterpart E2F or P/CAF polypeptide or peptide as a fusion with (e.g.) VP60, and involves a third expression cassette, which may be on a separate expression vector, from which a peptide or a library of peptides of diverse and/or random sequence may be expressed. A reduction in reporter gene expression (e.g. in the case of β-galactosidase a weakening of the blue colour) results from the presence of a peptide which disrupts the P/CAF/E2F interaction, which interaction is required for transcriptional activation of the β-galactosidase gene. Where a test substance is not peptidyl and may not be expressed from encoding nucleic acid within a said third expression cassette, a similar system may be employed with the test substance supplied exogenously.

When performing a two hybrid assay to look for substances which interfere with the interaction between two polypeptides or peptides it may be preferred to use mammalian cells instead of yeast cells. The same principles apply and appropriate methods are well known to those skilled in the art.

In preferred assays according to the present invention, the end-point of the assay, that is to say that which is determined in order to assess the effect of the test agent on the interaction of interest, is acetylation of E2F or a fragment, variant or derivative thereof.

Thus, a further aspect of the present invention provides an assay method including:

(a) bringing into contact a substance which includes at least a fragment of P/CAF which acetylates E2F, a substance which includes at least a fragment of E2F including a site acetylated by P/CAF, and a test compound; and (b) determining acetylation at said site.

Of course, any suitable variant or derivative of P/CAF and/or E2F may be employed in such an assay and any suitable fragments of E2F may be employed including any of the sites of acetylation, such as including one or more of the relevant lysines as discussed above (e.g. for E2F1 lys117, lys120 and/or lys125).

Another aspect of the present invention provides an assay method for a substance able to affect E2F acetylation, the method including:

(a) treating acetylated E2F with a test compound; and (b) determining acetylation of the E2F.

A still further aspect of the present invention provides an assay method for a substance able to affect E2F acetylation, the method including:

(a) treating with a test compound E2F which is not acetylated at one or more of the relevant positions noted above; and (b) determining acetylation of the E2F.

As noted, E2F may be acetylated at one or more residues, particularly one or more of the lysine residues which correspond to Lys117, Lys120 and/or Lys125 in E2F1.

Acetylation may be determined for example by immobilising E2F or a fragment, variant or derivative thereof, e.g. on a bead or plate, and detecting acetylation using an antibody or other binding molecule which binds the relevant site of acetylation with a different affinity when the site is acetylated from when the site is not acetylated. Such antibodies may be obtained by means of any standard technique as discussed elsewhere herein, e.g. using a acetylated peptide (such as a fragment of E2F). Binding of a binding molecule which discriminates between the acetylated and non-acetylated form of E2F or relevant fragment, variant or derivative thereof may be assessed using any technique available to those skilled in the art, which may involve determination of the presence of a suitable label.

Acetylation may also be assayed in solution, e.g. as described in Bannister and Kouzarides (1996), Nature, 384: 641–643. Briefly, protein substrate (~1 μg) and ~0.1 pmol of acetyltransferase are mixed to give a final volume of 30 μl in buffer IPH (50 mM Tris.HCl pH8.0, 150 mM NaCl, 5 mM EDTA, 0.5% [v/v] NP-40, 0.1 mM PMSF). Reactions are initiated by the addition of [14-C]-acetyl coA (1.85 kBq: 1.85 GBq/mmol; Amersham) and incubated at 30° C. for 10–45 min. The reaction products are then resolved by SDS-PAGE and viewed following fluorography of the gel. Alternatively, following SDS-PAGE, the resolved proteins can be Western blotted to a nitrocellulose membrane, which is then dried and exposed to film.

A further option is an in-gel activity assay, such as described by Brownell and Allis (1995), *Proc. Natl. Acad. Sci.*, 92: 6364–6368 or Mizzen, et al (1996), *Cell*, 87: 1261–1270. Samples may be crude cellular extracts, partially purified fractions, highly purified cellular proteins or bacterially produced and purified recombinant proteins. Before loading onto the activity gel the sample is made to 1×SDS-PAG loading buffer and boiled for 2 minutes. The gel is a standard Laemmli SDS-PAG except that purified protein substrate is added to the resolving gel to a final concentration of 1 mg/ml. Polymerisation of the gel is initiated using standard techniques, at which point the protein substrate becomes immobilized within the gel matrix. After adding the stacking gel, the samples are loaded and the gel run as a standard SDS-PAG. After the gel has run it is soaked, with gentle agitation, in 100 ml of wash buffer (50 mM Tris.HCl pH8.0, 0.1% β-mercaptoethanol) containing 20% (v/v) isopropanol for 20 minutes at room temperature. This washing step is repeated twice. Proteins in the gel are then denatured by washing in 100 ml of wash buffer containing 8M urea for 20 minutes at room temperature. This denaturing step is repeated twice. The gel is then soaked without agitation in 100 ml of wash buffer containing 0.04% tween-31 40 for 20 minutes at 4° C. This step is then repeated but for a duration of 12 hours, after which the gel is washed twice for a period of 20 minutes each time. After the final soak the gel/buffer is allowed to slowly come to room temperature. The gel is washed in wash buffer containing 10% (v/v) glycerol for 20 minutes at room temperature. The gel is then placed in a heat sealable bag and 3 ml of the same buffer containing 10 $\mu$Ci of [3H]-acetylCoA is added. The contents are thoroughly mixed, air bubbles removed and the bag sealed. The reaction is then performed by immersing the bag in a 30° C. water-bath for at least 30 minutes. Following the acetylation step, the gel is recovered and washed extensively in several 100 ml changes of gel destain solution (10% [v/v] methanol, 10% [v/v] acetic acid). This washing stage is performed at room temperature with agitation and should include an overnight wash.

An agent able to inhibit acetylation of E2F by P/CAF or other acetylase may include or other substance able to affect the catalytic properties of the enzymatically active site of the acetylase. An inhibitor of acetylation may interact with P/CAF or other acetylase within the acetylase domain. Residues within this domain are involved with interaction with E2F and catalysis of the acetylation. Residues outside of the domain may also be involved in interacting with E2F and agents which interfere with such interaction may affect the acetylation as discussed elsewhere herein.

Nucleic acid constructs in which a site recognised by E2F and at which, on binding when acetylated, E2F stimulates transcription from an operably-linked promoter, may be used to assess the effect a test substance has on E2F function, by determination of promoter activity. E2F binding sites for different members of the family have been established by PCR selection assays (Tao, et al, *Molecular and Current Biology*: Vol 17, No 12, 6994–7007. An example of a suitable promoter is that of the human cyclin E gene, a relevant biological target of E2F1. There is evidence that activation of this promoter by E2F1 is required by for cell cycle progression (Ohtani, et al, *PNAS:* 92, 12146–12150 and Botz, et al, Molecular and Cellular Biology: Vol 16, No 7, 3401–3409). (Agents in accordance with the present invention may be found which affect cyclin E transcription and cell cycle progression, and may be used to affect these.)

Thus a further assay method according to the present invention involves (a) providing E2F or a fragment, variant or analogue thereof able to activate transcription from a promoter including a E2F binding site, a test compound, and a reporter construct including a promoter which includes a E2F binding site and which is operably linked to a reporter sequence for transcription thereof, under conditions wherein, in the absence of the test compound being an inhibitor of E2F acetylation, the reporter sequence is transcribed;

(b) determining promoter activity.

P/CAF and/or other acetylase able to acetylate E2F may be included in the assay medium.

A further assay method of the present invention includes (a) providing E2F or a fragment thereof which is not acetylated at one or more of the relevant positions noted above, a test compound, and a reporter construct including a promoter which includes a E2F binding site and which is operably linked to a reporter sequence for transcription thereof, under conditions wherein if the test compound promotes acetylation of E2F the reporter sequence is transcribed;

(b) determining promoter activity.

P/CAF and/or other acetylase able to acetylate E2F may be included in the assay medium.

A further assay method according to the present invention includes (a) providing E2F or a fragment, variant or analogue thereof able to interact with P/CAF and able to activate transcription from a promoter including a E2F binding site, P/CAF or a fragment, variant or analogue thereof able to interact with E2F, a test compound, and a reporter construct including a promoter which includes a E2F binding site and which is operably linked to a reporter sequence for transcription thereof, under conditions wherein, in the absence of the test compound being an inhibitor of interaction between P/CAF and E2F, the reporter sequence is transcribed;

(b) determining promoter activity.

The test compound may promote interaction between P/CAF and E2F and enhance transcription of the reporter sequence.

The interaction between P/CAF and E2F may include acetylation of E2F.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific MRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production.

In such a construct, the promoter is operably linked to a gene, e.g. a coding sequence. Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Thus, nucleic acid constructs comprising a promoter and a reporter gene may be employed in screening for a substance able to modulate the transcriptional activator activity of E2F on the promoter. For therapeutic purposes, e.g. for treatment of cancer, a substance able to inhibit expression of the promoter, i.e. antagonise the stimulator function of E2F, may be sought. A method of screening for ability of a substance to modulate activity of E2F may comprise contacting an expression system, such as a host cell, containing a nucleic acid construct as discussed with a test or candidate substance and determining expression of the reporter gene. The level of expression in the presence of the test substance may be compared with the level of expression in the absence of the test substance. A difference in expression in the presence of the test substance may indicate ability of the substance to modulate E2F function.

A promoter construct may be introduced into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed then analysed.

Preliminary assays in vitro may be followed by, or run in parallel with, in vivo assays.

Of course, the person skilled in the art will design any appropriate control experiments with which to compare results obtained in test assays.

Performance of an assay method according to the present invention may be followed by isolation and/or manufacture and/or use of a compound, substance or molecule which tests positive for ability to modulate interaction between P/CAF and E2F and/or modulate P/CAF or E2F activity or a mediated activity. Following identification of a suitable agent it may be investigated further. Furthermore, it may be manufactured and/or used in preparation, i.e. manufacture or formulation, of a composition such as a medicament, pharmaceutical composition or drug. These may be administered to individuals.

The amount of test substance or compound which may be added to an assay of the invention will normally be determined by trial and error depending upon the type of compound used. Typically, from about 0.001 nM to 1 mM or more concentrations of putative inhibitor compound may be used, for example from 0.01 nM to 100 μM, e.g. 0.1 to 50 μM, such as about 10 μM. Greater concentrations may be used when a peptide is the test substance. Even a molecule which has a weak effect may be a useful lead compound for further investigation and development.

Compounds which may be used may be natural or synthetic chemical compounds used in drug screening programmes. Extracts of plants which contain several characterised or uncharacterised components may also be used.

Antibodies directed to the site of interaction in either protein form a further class of putative inhibitor compounds.

Candidate inhibitor antibodies may be characterised and their binding regions determined to provide single chain antibodies and fragments thereof which are responsible for disrupting the interaction. The term "antibody molecule" may generally be used to cover antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

As noted above, antibody molecules may be used for determining whether or not a peptide or polypeptide (e.g. E2F or fragment thereof) is acetylated, provided the relevant antibody molecule is able to discriminate between acetylated and non-acetylated forms of the peptide.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Antibodies may also be used in purifying and/or isolating a polypeptide or peptide according to the present invention, for instance following production of the polypeptide or peptide by expression from encoding nucleic acid therefor. Antibodies may be useful in a therapeutic context (which may include prophylaxis) to disrupt P/CAF and E2F interaction with a view to inhibiting their activity. Antibodies can for instance be micro-injected into cells, e.g. at a tumour site, subject to radio- and/or chemo-therapy (as discussed already above). Antibodies may be employed in accordance with the present invention for other therapeutic and non-therapeutic purposes which are discussed elsewhere herein.

Other candidate inhibitor compounds may be based on modelling the 3-dimensional structure of a polypeptide or peptide fragment and using rational drug design to provide potential inhibitor compounds with particular molecular shape, size and charge characteristics.

A compound found to have the ability to affect P/CAF and/or E2F activity has therapeutic and other potential in a number of contexts, as discussed. For therapeutic treatment such a compound may be used in combination with any other active substance, e.g. for anti-tumour therapy another anti-tumour compound or therapy, such as radiotherapy or chemotherapy. In such a case, the assay of the invention, when conducted in vivo, need not measure the degree of modulation of interaction between E2F and P/CAF (or appropriate fragment, variant or derivative thereof) or of modulation of E2F acetylation or activity caused by the compound being tested. Instead the effect on transition of cells into S-phase, oncogenesis in tissue culture and/or induction of cell death by apoptosis may be determined. It may be that such a modified assay is run in parallel with or subsequent to the main assay of the invention in order to confirm that any such effect is as a result of the inhibition of interaction between P/CAF and E2F caused by said inhibitor compound and not merely a general toxic effect.

Thus, an agent identified using one or more primary screens (e.g. in a cell-free system) as having ability to interact with P/CAF and/or E2F and/or modulate activity of P/CAF and/or E2F may be assessed further using one or more secondary screens. A secondary screen may involve testing for a biological function of E2F as noted above (e.g. induction of S-phase or apoptosis).

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the interaction between P/CAF and E2F. Examples of such analogues include chemical compounds which are modelled to resemble the three dimensional structure of the P/CAF or E2F domain in the contact area, and in particular the arrangement of the key amino acid residues as they appear in P/CAF or E2F.

In a further aspect, the present invention provides the use of the above substances in methods of designing or screening for mimetics of the substances.

Accordingly, the present invention provides a method of designing mimetics of P/CAF or E2F having the biological activity of E2F or P/CAF binding or inhibition, the activity of allosteric inhibition of E2F or P/CAF and/or the activity of modulating, e.g. inhibiting, P/CAF/E2F interaction, said method comprising:

(i) analysing a substance having the biological activity to determine the amino acid residues essential and important for the activity to define a pharmacophore; and, (ii) modelling the pharmacophore to design and/or screen candidate mimetics having the biological activity.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduced those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. some peptides may not be well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

The present invention further provides the use of a peptide which includes a sequence as disclosed, or a derivative, active portion, analogue, variant or mimetic, thereof able to interact with P/CAF or E2F and/or modulate, inhibit or potentiate, interaction between P/CAF and E2F and/or modulate, inhibit or potentiate, P/CAF and/or E2F activity, in screening for a substance able to interact with E2F and/or P/CAF, and/or modulate, inhibit or potentiate, interaction between P/CAF and E2F, and/or modulate P/CAF and/or E2F activity.

Generally, such a substance according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologicaly acceptable excipients. As noted below, a composition according to the present invention may include in addition to an modulator compound as disclosed, one or more other molecules of therapeutic use, such as an anti-tumour agent.

The present invention extends in various aspects not only to a substance identified as a modulator of P/CAF and E2F interaction and/or P/CAF or E2F-mediated activity, property or pathway, in accordance with what is disclosed herein, but also a pharmaceutical composition, medicament, drug or other composition comprising such a substance, a method comprising administration of such a composition to a patient, e.g. for a purpose discussed elsewhere herein, which may include preventative treatment, use of such a substance in manufacture of a composition for administration, e.g. for a purpose discussed elsewhere herein, and a method of making a pharmaceutical composition comprising admixing such a substance with a pharmaceutically acceptable excipient, vehicle or carrier, and optionally other ingredients.

A substance according to the present invention such as an inhibitor of P/CAF and E2F interaction may be provided for use in a method of treatment of the human or animal body by therapy which affects an P/CAF or E2F-mediated activity in cells, e.g. tumour cells. Other purposes of a method of treatment employing a substance in accordance with the present invention are discussed elsewhere herein.

Thus the invention further provides a method of modulating an P/CAF and/or E2F-mediated activity, e.g. for a purpose—discussed elsewhere herein, which includes administering an agent which modulates, inhibits or blocks the interaction of P/CAF with E2F protein, such a method being useful in treatment where such modulation, inhibition or blocking is desirable, or an agent which increase, potentiates or strengthens interaction of P/CAF with E2F, useful in treatment where this is desirable.

The invention further provides a method of treatment which includes administering to a patient an agent which interferes with the interaction of P/CAF with E2F. Exemplary purposes of such treatment are discussed elsewhere herein.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, eg in a viral vector (a variant of the VDEPT technique—see below). The vector may targeted to the specific cells to be treated, or it may contain regulatory elements which are switched on more or less selectively by the target cells.

The agent (e.g. small molecule, mimetic) may be administered in a precursor form, for conversion to the active form by an activating agent produced in, or targeted to, the cells to be treated. This type of approach is sometimes known as ADEPT or VDEPT, the former involving targeting the activator to the cells by conjugation to a cell-specific antibody, while the latter involves producing the activator, e.g. an enzyme, in a vector by expression from encoding DNA in a viral vector (see for example, EP-A-415731 and WO 90/07936).

An agent may be administered in a form which is inactive but which is converted to an active form in the body. For instance, the agent may be phosphorylated (e.g. to improve solubility) with the phosphate being cleaved to provide an active form of the agent in the body.

A composition may be administered alone or in combination with other treatments, either simultaneously or sequentially dependent upon the condition to be treated, such as cancer, virus infection or any other condition in which a P/CAF or E2F-mediated effect is desirable.

Nucleic acid according to the present invention, encoding a polypeptide or peptide able to modulate, e.g. interfere with, P/CAF and E2F interaction and/or induce or modulate activity or other P/CAF or E2F-mediated cellular pathway or function, may be used in methods of gene therapy, for instance in treatment of individuals, e.g. with the aim of preventing or curing (wholly or partially) a disorder or for another purpose as discussed elsewhere herein.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A polypeptide, peptide or other substance able to modulate or interfere with the interaction of the relevant polypeptide, peptide or other substance as disclosed herein, or a nucleic acid molecule encoding a peptidyl such molecule, may be provided in a kit, e.g. sealed in a suitable container which protects its contents from the external environment. Such a kit may include instructions for use.

Various further aspects and embodiments of the present invention will be apparent to those skilled in the art in view of the present disclosure. Certain aspects and embodiments of the invention will now be illustrated by way of example.

All documents mentioned anywhere herein are incorporated by reference.

EXPERIMENTAL

Experiment 1

An important regulator of the cell cycle, the E2F1 transcription factor, was found to be acetylated in vitro by the P/CAF acetyltransferase.

Recombinant GST-E2F-1 or BSA or GST proteins were incubated with $^3$HAcetylCoA in the presence or absence (-) of P/CAF and CBP, during 30 min. at 30° C. After that the reaction products were loaded in a 10% PAA gel, this was fluorographed, dried and exposed over night. In the lane corresponding to GST-E2F-1 incubation with P/CAF a band corresponding to acetylated GST-E2F-1 protein was seen, but not in any other of the lanes.

Experiment 2

A series of deletions of human E2F1 were used to show acetylation of the protein in the region between amino acids 89 and 287.

Different GST-E2F-1 deletion proteins (the portions of E2F corresponding to amino acids 380–432, 358–432, 287–432 and 89–432), as well as GST-EMA and GST-DP1 proteins were incubated with $^3$HAcetylCoA in the presence of P/CAF for 30 min. at 30° C. The reaction products were loaded in a 105 PAA gel, and this was fluorographed, dried and exposed over night. A band corresponding to acetylated GST-E2F-1 protein was seen in only one lane, corresponding to incubation of the portion of E2F-1 of amino acids 89–432, indication acetylation taking place between amino acids 89 and 287 of E2F-1.

Experiment 3

A series of point mutations of human E2F1 were used to show the acetylation of three closely spaced lysines at position 117, 120 and 125 has important biological significance. Mutation of all three lysines to arginine resulted in an E2F1 protein which can no longer be acetylated by P/CAF.

Point mutations were made where Lys (161, 164), (182, 183, 185) and (117, 120, 125) on GST-E2F-1 were changed to alanines, using a site directed mutagenesis Kit from Stratagene. The mutated proteins were expressed in E. Coli and subjected to acetylation by incubating them with P/CAF in the presence of $^3$HAcetylCoA for 30 min. at 30° C. After that they were separated in a 10% PAA gel, this was fluorographed, dried and exposed over night at −70° C. A band corresponding to acetylated GST-E2F-1 protein was seen in all lanes except for that corresponding to incubation of E2F-1 K (117, 120, 125).

Experiment 4

Acetylation of E2F1 by P/CAF was shown to increase the ability of E2F1 to activate transcription.

A reporter plasmid containing E2F binding sites upstream from a CAT reporter was introduced into U205 cells along with wild-type E2F or mutant E2F in which lysines 117, 120 and 125 were changed to arginine. Each transfection also contained DP1 (which co-operates with E2F in DNA binding).

When P/CAF was included in the transfection, the wild-type E2F was stimulated in activity, but the mutant was not.

If a mutant P/CAF was included, mutated in the HAT domain to abolish acetyltransferase activity, the stimulation of wild-type E2F was not seen.

These results show that P/CAF stimulates the activation capacity of E2F, and that this is by virtue of the ability of P/CAF to acetylate E2F at lysine residues 117, 120 and 125.

Thus, preventing acetylation of E2F may be used to affect its biological function. Since E2F1, E2F2 and E2F3 are able to induce S-phase and cell transformation via the activation potential, disruption of E2F acetylation (in particular of E2F1, E2F2 or E2F3) may be used to inhibit cell proliferation. Also, given the role of E2F in inducing apoptosis, modulating E2F acetylation may be used to potentiate cell killing.

Experiment 5

By means of Western blotting using an antibody which recognises aceylated lysine residues, E2F was shown to be acetylated in U205 cells. E2F was precipitated with an E2F-1 specific antibody and then Western blotted with an anti-acetylated lysine antibody.

Experiment 6

Co-immunoprecipitation was used to show that P/CAF binds E2F1 in vivo.

P/CAF tagged with a Flag was transfected into cells. E2F-1 was then immunoprecipitated and the Flag-tagged P/CAF was detected by a Western blot. No band was detected in the absence of P/CAF or when truncated P/CAF (residues 352–832) was employed.

Immunoprecipitation Methodology

Cells were harvested by trypsinization, washed twice with ice-cold PBS and resuspended in 500 µl RIPA buffer (150 mM NaCl, 10.0 % NP-40, 0.5% DOC, 0.1% SDS, 50 mM Tris-HCl pH 8.0) supplemented with a cocktail of protease inhibitors (Complete, Boehringer Mannheim). After 30 min incubation on ice the whole cell extracts were clarified by centrifugation at 12,000 g for 10 min, and the supernatant precleared with 30 µl protein A/G sepharose at 4° C. for 30 min. 2 µg of polyclonal anti-E2F1 antibody C20 (Santa Cruz) were added to the extracts and rocked at 4° C. overnight. Then 30 µl protein A/G sepharose were added for another 2 hr at 4° C. After 4 extensive washes in RIPA buffer, the beads were boiled in SDS containing sample buffer. Proteins were separated on a 12.5% SDS-PAGE and transferred to nitrocellulose membrane by standard procedures. For the detection of acetylated E2F1 in vivo, Western blot analysis was performed with an polyclonal anti-AcLys antibody. For pulse chase analysis, the blots were exposed to X-ray (Biomax MS, Kodak) and the intensity of [$^{35}$S] labeled E2F protein was measured with the NIH Image 1.61 program and calculated in comparison to the protein present at time zero.

Experiment 7

Acetylation of E2F by P/CAF was shown to lead to an increase in ability of E2F to bind DNA, as determined by means of a DNA mobility-shift assay performed using recombinant, bacterially expressed E2F and a DNA oligonucleotide with an E2F1 binding site.

For electrophoretic mobility shift assay (EMSA) His-tagged E2F1, GST-tagged E2F1 arginine mutant and GST-tagged DP1 were synthesized in *E. coli*, purified on Ni NTA-agarose or glutathione sepharose and eluted from the beads. E2F1 and E2F1 mutant were acetylated in IPH buffer in the presence of 2 mM acetyl coA and GST-PCAF (352–658) protein and then used for EMSA. 25 µl DNA binding reaction mixture contained binding buffer (50 mM KCl, 10 mM MgCl$_2$, 0.5 mM DTT, 20 mM HEPES pH 7.5), 100 ng poly(dA)-poly(dT), 25 µg bovine serum albumine, 0.5 µg sonicated salmone sperm DNA, approximately 50–200 ng fusion proteins and 50 fmol $^{32}$P-labeled oligonucleotide (modified E2F1 binding site of DHFR gene promoter). Binding reactions were performed at room temperature for 10 min. The reaction products were separated in a 4% polyacrylamid gel run in 0.25×TBE (22.5 mM Trisborate, 0.5 mM EDTA). Subsequently the gel was dried and exposed to X-ray.

Experiment 8

Experiment 7 was repeated except recombinant E2F was used in which residues 117, 120 and 125 had been changed to arginine.

Unlike the wild-type acetylated E2F1 (see Experiment 7), the mutant—unacetylated—E2F1 was not stimulated by P/CAF in DNA binding.

Experiment 9

P/CAF was found to stabilised E2F protein. Introduction of P/CAF into cells was found to lead to the presence of elevated levels of E2F1, as seen by pulse chase labelling of E2F and Western blot. The pulse chase shows that in the presence of P/CAF the E2F protein has a longer half-life.

293T cells were transfected overnight using the calcium phosphate method. 24 h after removal of the transfection precipitate, the cells were washed twice with PBS and starved for 1 hr in methionine/cysteine free medium. Subsequently, 0.2 mCi of [$^{35}$S]methionine/cystein (NEN) was added to each flask, and the cells were incubated for 2 hr. After the labeling, the cells were harvested for time zero or incubated with normal medium supplemented with 10 fold excess of nonradioactive methionine and cysteine for 1, 3 and 5 hr and harvested thereafter. Equal amounts of radio active lysate were used for immunoprecipitation as described above.

The stabilisation was shown to be mediated by the acetyltransferase activity of P/CAF: a P/CAF mutant lacking active HAT domain (ΔHAT) did not stabilise E2F. The stabilisation was also seen on introduction of RB (retinoblastoma protein), and effect which has been reported before and serves as a positive control.

What is claimed is:

1. An assay method for an agent which affects E2F acetylation, the method including:
   (a) treating an acetylated E2F polypeptide or an acetylated E2F peptide with a test compound, or
   (b) treating with a test compound an E2F polypeptide or an acetylated E2F peptide which comprises one or more lysine residues corresponding to those found at positions 117, 120 and 125 in wild-type E2F1, in which polypeptide or peptide one or more of said lysines is not acetylated, or
   (c) bringing into contact a substance which includes a P/CAF polypeptide which acetylates E2F, a substance which includes an E2F polypeptide or an E2F peptide including a site acetylated by P/CAF, and a test compound;
   and, following step a, b or c,
   (d) determining acetylation of the E2F polypeptide or E2F peptide,
   wherein said E2F polypeptide has a sequence selected from the group consisting of the human E2F1, E2F2, E2F3, E2F4 and E2F5 sequences,
   said E2F peptide is a peptide fragment of a sequence selected from the group consisting of the human E2F1, E2F2, E2F3, E2F4 and E2F5 sequences, and;
   said P/CAF polypeptide has the sequence of human P/CAF.

2. An assay method for an agent which affects E2F activity, the method including:
   (a) bringing into contact E2F and a test compound; and
   (b) determining E2F activity in the presence and absence of a P/CAF polypeptide which acetylates E2F,
   wherein E2F has a sequence selected from the group consisting of the human E2F1, E2F2, E2F3, E2F4 and E2F5 sequences and said P/CAF polypeptide has the sequence of human P/CAF.

3. An assay method for an agent which affects E2F activity, the method comprising:
   (a) providing an E2F polypeptide which activates transcription from a promoter including an E2F binding site, a test compound, and a reporter construct including a promoter which includes an E2F binding site and which is operably linked to a reporter sequence for transcription thereof, under conditions wherein, in the absence of the test compound being an inhibitor of E2F acetylation, the reporter sequence is transcribed, or
   (b) providing an E2F polypeptide which activates transcription from a promoter including an E2F binding site, which polypeptide comprises one or more lysine residues corresponding to those found at positions 117, 120 and 125 in wild-type E2F1, and in which polypeptide or peptide one or more of said lysines is not acetylated, a test compound, and a reporter construct including a promoter which includes an E2F binding site and which is operably linked to a reporter sequence for transcription thereof, under conditions wherein if the test compound promotes acetylation of E2F the reporter sequence is transcribed, or
   (c) providing an E2F polypeptide which interacts with P/CAF and activates transcription from a promoter including an E2F binding site, a P/CAF polypeptide which interacts with E2F, a test compound, and a reporter construct including a promoter which includes an E2F binding site and which is operably linked to a reporter sequence for transcription thereof, under conditions wherein, in the absence of the test compound being an inhibitor of interaction between P/CAF and E2F, the reporter sequence is transcribed;
   and, following step a, b or c
   (d) determining promoter activity,
   wherein said E2F polypeptide has a sequence selected from the group consisting of human E2F1, E2F2, E2F3, E2F4 and E2F5 sequence; and said P/CAF polypeptide has the sequence of human P/CAF.

4. An assay method for an agent which modulates interaction between P/CAF and E2F, the method including:
- (a) bringing into contact a first substance including a P/CAF polypeptide or a P/CAF peptide, a second substance including an E2F polypeptide or an E2F peptide, and a test compound under conditions in which, if of the test compound does not disrupt the interaction between P/CAF and E2F, the first and second substances interact; and
- (b) determining interaction between the first and second substances,
- wherein said E2F polypeptide has sequence selected from the group consisting of the human E2F1, E2F2, E2F3, E2F4 and E2F5 sequences;
- said E2F peptide is a peptide fragment of a sequence selected from the group consisting of the human E2F1, E2F2, E2F3, E2F4 and E2F5 sequences; and,
- said P/CAF polypeptide has the sequence of human P/CAF.

5. An assay method for an agent which affects one or more of (i) ability of E2F to stimulate transcription, (ii) induction of S-phase in cells, (iii) oncogenicity of cells, and/(iv) induction of apoptosis in cells, the method comprising:
- (a) bringing into contact a P/CAF polypeptide and a test compound, and
- (b) determining P/CAF acetyltransferase activity;
- wherein a test compound which inhibits P/CAF acetyltransferase activity is identified as a candidate said agent,
- wherein E2F is selected from the group consisting of human E2F1, E2F2, E2F3, E2F4 and E2F5; and, said P/CAF polypeptide has the sequence of human P/CAF.

6. A method according to claim 5 comprising determining acetylation of E2F by said P/CAF polypeptide.

7. A method according to claim 5 comprising determining E2F activity.

8. A method according to claim 5 wherein a test compound which inhibits P/CAF acetyltransferase activity is further tested for ability to affect one or more of (i) ability of E2F to stimulate transcription, (ii) induction of S-phase in cells, (iii) oncogenicity of cells, and (iv) induction of apoptosis in cells.

9. An assay method for an agent which interacts with a region of P/CAF or a region of E2F, which region of P/CAF interacts with E2F and which region of E2F interacts with P/CAF, a said agent which interacts with a said region being a candidate modulator of interaction between P/CAF and E2F, the method including:
- (a) bringing into contact a substance which includes a P/CAF peptide which interacts with E2F, or which includes an E2F peptide which interacts with P/CAF, and a test compound; and
- (b) determining interaction between said substance and the test compound,
- wherein said E2F polypeptide has a sequence selected from the group consisting of the human E2F1, E2F2, E2F3, E2F4 and E2F5 sequences;
- said E2F peptide is a peptide fragment of a sequence selected from the group consisting of human E2F1, E2F2, E2F3, E2F4 and E2F5 sequences; and,
- said P/CAF polypeptide has the sequence of human P/CAF.

10. A method according to any one of claims 1, 2, 3, 4, 5 and 9 further comprising formulating a said agent into a composition comprising at least one additional component.

* * * * *

UNITED STATES PATENT AND TRADEMARK OFFICE
CERTIFICATE OF CORRECTION

PATENT NO. : 6,890,709 B1  Page 1 of 1
APPLICATION NO. : 09/700417
DATED : May 10, 2005
INVENTOR(S) : Kouzarides It is certified that error appears in the above-identified patent and that said Letters Patent is hereby corrected as shown below:

Title page,

"(30)     Foreign Application Priority Data"

change:

May 17, 2000   (DE) ……………………………….. 9810582 to read as:

May 15, 1998   (GB) …………………………….. 9810562.0

Signed and Sealed this

First Day of January, 2008

JON W. DUDAS
*Director of the United States Patent and Trademark Office*